United States Patent
Delcomyn et al.

(10) Patent No.: US 7,582,594 B2
(45) Date of Patent: Sep. 1, 2009

(54) DIOXIRANE FORMULATIONS FOR DECONTAMINATION

(75) Inventors: Carrie Delcomyn, Lynn Haven, FL (US); Jean Renard, Panama City, FL (US); William Wallace, Panama City, FL (US); Michael Henley, Panama City, FL (US)

(73) Assignee: Applied Research Associates, Inc., Albuqurque, NM (US)

( * ) Notice: Subject to any disclaimer, the term of this patent is extended or adjusted under 35 U.S.C. 154(b) by 242 days.

(21) Appl. No.: 10/687,864

(22) Filed: Oct. 17, 2003

(65) Prior Publication Data

US 2005/0085402 A1    Apr. 21, 2005

(51) Int. Cl.
    C11D 1/00    (2006.01)
    C11D 3/10    (2006.01)
    C11D 3/20    (2006.01)
    C11D 3/39    (2006.01)
    C11D 3/43    (2006.01)

(52) U.S. Cl. .................. 510/372; 510/383; 510/505; 510/506; 510/509

(58) Field of Classification Search ............... 510/372, 510/383, 505, 506, 509
    See application file for complete search history.

(56) References Cited

U.S. PATENT DOCUMENTS

| | | | |
|---|---|---|---|
| 4,001,131 A | | 1/1977 | Montgomery |
| 4,485,028 A * | | 11/1984 | King ............... 510/239 |
| 4,576,738 A * | | 3/1986 | Colodney et al. ....... 510/424 |
| 4,850,729 A | | 7/1989 | Kramer et al. |
| 5,078,902 A | | 1/1992 | Antelman |
| 5,098,582 A | | 3/1992 | Antelman |
| 5,186,946 A | | 2/1993 | Vallieres |
| 5,366,593 A * | | 11/1994 | Lee et al. ............... 162/72 |
| 5,403,549 A * | | 4/1995 | McNeil et al. ........... 422/29 |
| 5,437,686 A | | 8/1995 | Heffner et al. |
| 5,501,802 A | | 3/1996 | Thorp et al. |
| 5,621,118 A * | | 4/1997 | Jones et al. ........... 549/200 |
| 6,046,150 A * | | 4/2000 | Choy et al. ........... 510/376 |
| 6,143,088 A * | | 11/2000 | Lion et al. ............ 134/2 |
| 6,224,779 B1 | | 5/2001 | Spector |
| RE37,207 E | | 6/2001 | Cronce |
| 6,245,957 B1 | | 6/2001 | Wagner et al. |
| 6,284,144 B1 | | 9/2001 | Itzhak |
| 6,302,969 B2 * | | 10/2001 | Moster et al. ............ 134/40 |
| 6,369,288 B1 | | 4/2002 | Brown |
| 6,566,574 B1 | | 5/2003 | Tadros et al. |
| 6,569,353 B1 | | 5/2003 | Giletto et al. |

* cited by examiner

*Primary Examiner*—Gregory R Del Cotto
(74) *Attorney, Agent, or Firm*—Dinsmore & Shohl, LLP; Monika J. Hussell

(57) ABSTRACT

A universal decontamination formulation is disclosed based on the in situ generation dioxirane(s) under non-corrosive neutral conditions for the neutralization of chemical and biological warfare (CBW) agents. The composition relates to the generation of dioxiranes by mixing a monopersulfate-containing compound in the presence of a ketone in water buffered with a carbonate-type buffer, producing a pH neutral formulation that provides effective reactivity towards CBW agents over a wide range of temperatures.

21 Claims, No Drawings

DIOXIRANE FORMULATIONS FOR DECONTAMINATION

FEDERAL RESEARCH STATEMENT

The U.S. Government has a paid-up license in this invention and the right in limited circumstances to require the patent owner to license others on reasonable terms as provided for by the terms of contract F0863798C6002 awarded by the United States Department of the Air Force, Air Training and Education Command.

FIELD OF THE INVENTION

The present invention relates to providing a universal decontaminating solution for the rapid neutralization of chemical and biological warfare (CBW) agents. More specifically, a method is described for use of an in situ generated dioxirane formulation by mixing a monopersulfate compound in the presence of a ketone in water, buffered with a carbonate-type buffer, to produce a pH neutral solution that is effectively reactive towards CBW agents over a wide range of temperatures.

BACKGROUND OF THE INVENTION

Recent world events involving terrorist activities have increased the need to develop an environmentally friendly universal decontaminating solution that possesses non-corrosive and non-toxic properties for the rapid neutralization of lethal chemical and biological warfare (CBW) agents. This need is particularly apparent in military operations in which large area decontamination would be required for aircraft, tanks, carrier ships, facilities, equipment, and terrain, as well as related civilian or homeland defense operations that would involve decontamination efforts by first-responder personnel.

Decontamination solutions presently available for the destruction of CBW agents include Super Tropical Bleach (STB), a highly corrosive hypochlorite-based alkaline solution, and DS2, which possesses highly toxic ingredients of diethylenetriamine and ethylene glycol monomethyl (EGM) ether. These decontaminants have the drawbacks in that they present hazards to the handler(s) and surface materials, as well as adversely impacting the environment, and generate significant waste that requires unique disposal.

Efforts to develop more user-friendly decontaminants have focused on using strong oxidant applications such as ozone, titanium dioxide catalyzed photolysis, organic and inorganic peracids, activated hydrogen peroxide, and peroxygen compounds. For example, U.S. Pat. No. 4,850,729 discloses a decontaminating formulation utilizing "per-salts" such as percarbonate, perborate, persilicate or perphosphate, in dry or aqueous forms, for the purpose of rendering active hydrogen peroxide species. Iron bearing clays were also incorporated to serve as activators for hydrogen peroxide to create reactive radical species, as well as providing thickening properties to the formulation. Similarly, U.S. Pat. No. 6,245,957 describes a formulation in which potassium bicarbonate is mixed with urea hydrogen peroxide to create a peracid of percarbonate to effectively degrade chemical warfare agents. Although both inventions make use of peracid oxidants, neither reveals effectiveness toward biological agents.

The uses of either hydrogen peroxide, or a peroxygen compound such as monopersulfate, have been described as the reactive oxidative species within other multi-component formulations that target decontamination of both chemical and biological agents. U.S. Pat. No. 6,369,288 discloses a surfactant system that contains a peroxygen compound in conjunction with a detergent bleach activator for the purpose of generating peroxycarboylic acid as an active ingredient. Another surfactant based formulation disclosed in U.S. Pat. No. 6,566,574 is the combination of a water-soluble polymer, a corrosion inhibitor, a fatty alcohol, and a catalyst together with the reactive oxidative component, but functions under slightly alkaline pH conditions.

Similar to the chemistry found in U.S. Pat. No. 4,850,729, U.S. Pat. No. 6,569,353 utilizes a ferrous iron bearing salt as an activator for hydrogen peroxide to generate powerful hydroxyl radicals in conjunction with the use of a monopersulfate compound. However, this particular formulation is prepared under acidic conditions in the presence of phosphate and is based in fumed silica media.

As reported by Yang et al. Chem. Rev. 92, 1729 (1992), monopersulfate alone has been shown to be reactive towards the chemical agents of mustard gas (HD) and VX, but only under aggressive acidic conditions. A significant amount of a dissolving agent was also needed in this case to solubilize mustard in solution. U.S. Pat. No. 5,186,946 described the use of monopersulfate for biological disinfection for viruses, bacteria, and spores, by combining with sulfamic and malic acids and polyethylene glycol, but also under acidic conditions.

Overall, the particular formulations described above fail to disclose the inclusion of a ketone-containing compound in the presence of monopersulfate to generate dioxirane oxidative species.

Montgomery J. Am. Chem. Soc. 96, 7820 (1974) is credited with the first observation of in situ generation of dioxirane species, in which ketones were shown to catalyze the decomposition of monopersulfate in solution, as well as enhance oxidative reactivity towards select chemical substrates. Murray Chem. Rev. 89, 1187 (1989) and Adam et al. Acc. Chem. Res. 22, 205 (1989) since provided an extensive cross-reference list on the synthetic transformations of numerous substrates from both preparations of in situ generated dioxiranes and dioxiranes isolated in neat ketone solvents, thereby demonstrating unique and powerful oxidative selectivity and reactivity.

Related dioxirane patents include U.S. Pat. Nos. 5,437,686 and 4,001,131, from the textile industry. Each discloses different formulations comprising a peroxygen compound and a diketone for the generation of dioxirane. The diketones for these particular applications were required as opposed to monoketones in that they demonstrated superior inhibition of dye transfer between fabrics during the cleaning process.

More relevant is U.S. Pat. No. 5,403,549 which discloses a method and composition for disinfecting matter or materials contaminated with bacteria, consisting of a mixture of monopersulfate and a carbonyl-containing compound, identified as either a ketone or aldehyde, for producing dioxirane. Carbonyl-containing compounds tested in the patent included acetone, 2-pentanone, 4-hydroxy-4-methyl-2-pentanone, and camphorsulfonic acid. The '549 patent is limited in its disclosure and application, specifically stating that the use of phosphate buffer within a neutral pH range actually inhibits the biocidal activity of a dioxirane solution towards substrates, and discloses formulations only in room temperature conditions (20°-25° C.) to effectively sterilize equipment. Rather, the '549 formulation requires a buffer utilized within an acidic range of about pH 4 to achieve effective disinfection. Application towards toxic chemical substrates was also not described.

To date, dioxirane-producing formulations have not been utilized in an effective manner under non-corrosive, neutral conditions in the presence of carbonate-type buffers to facilitate degradation of viscous CBW agents. The novelty of the disclosure herein is that powerful oxidative species of dioxirane can be generated rapidly in a cost-effective manner with the main by-products of reaction consisting of environmentally benign carbonate and sulfate salts, thereby aiming to provide an effective CBW agent decontaminating formulation that eliminates, or greatly minimizes the impacts of toxicity and corrosiveness to materials.

SUMMARY OF THE INVENTION

Accordingly, it is an object of the present invention to provide a universal decontaminating solution for the rapid neutralization of CBW agents at a range of temperatures and neutral conditions based on the generation of dioxiranes.

Dioxiranes are readily produced by mixing alkali metal monopersulfate (hereafter referred to as monopersulfate or monopersulfate compound) with a ketone-containing compound in water buffered with a carbonate-type compound, also preferably with the addition of co-solvent and surfactant, to produce an effective neutral-based decontaminating solution within a range of pH 5 to 9. The use of a carbonate-type buffer in our formulation is an improvement of prior art in that U.S. Pat. No. 5,403,549 teaches that the dioxirane formulation was unsuccessful at effective sterilization of biologicals in the presence of buffer within the aforementioned pH range, and that acidic pH was required to effect sterilization.

The solution of the present invention preferably comprises at least one co-solvent to facilitate solvation of the reagents in the formulation, and/or at least one surfactant to increase the adhesion properties of the solution upon contact with contaminated surface materials, thereby enhancing the effectiveness of the dioxirane against viscous and/or thickened CBW agents. Application of the present invention thereby provides rapid neutralization of agents through oxidative and hydrolysis mechanisms enhanced through solvation and wetting properties of the solution when placed in contact with surfaces contaminated with agents.

DETAILED DESCRIPTION OF THE PREFERRED EMBODIMENTS

The water-based composition of this invention includes monopersulfate and a ketone-containing compound in the presence of a carbonate-type buffer, and preferably includes at least one co-solvent and at least one surfactant.

Alkali metal monopersulfate is formed by the neutralization of Caro's acid ($H_2SO_5$), and can be found in the form of potassium monopersulfate ($KHSO_5$), and in the form of a triple salt with formula $2KHSO_5 \cdot KHSO_4 \cdot K_2SO_4$, manufactured and sold by Dupont under the trademark Oxone®.

Alkali metal salts of bicarbonate, such as sodium bicarbonate, are preferred for use in the formulation of the invention to buffer the monopersulfate and water to a neutral pH; however, other alkali metal salt forms of carbonate are also suitable for use in the composition of the present invention. Suitable ketones for use in the generation of dioxirane in combination with the monopersulfate include, but are not limited to, acetone, 2-butanone, 2-pentanone, 2-hydroxy-4-methyl-2-pentanone, hexafluoroacetone, trifluoroacetone, acetophenone, camphorsulfonic acid, and levulinic acid. Acetonitrile, propylene carbonate, propylene glycol, polypropylene glycol and/or tert-butanol are preferred co-solvents to facilitate solvation of the reagents, and surfactants tetrabutylammonium hydrogen sulfate (TBAHS), Triton-X, and/or cetyltrimethylammonium (CTMA) chloride are preferred to facilitate wetting properties of the formulation.

All reagents of the present invention are commercially available and can be readily formulated with tap water.

To begin preparation of the dioxirane decontaminant of the present invention, a solution of about 0.05-20% w/v carbonate-type buffer, dissolved in water, is prepared to which 0.1-40% w/v monopersulfate is added such that the resulting solution is in the range of pH 5 to 9. After mixing for 1-20 minutes, 0.1-40% v/v of a ketone is added for generation of the dioxirane. One or more co-solvents at a concentration within the range of 0.01-40% v/v, and 0.01-15% w/v of one or more surfactants, may be added to the formulation either prior to or after addition of the ketone(s), providing the additional solvation and surfactant wetting properties to the preferred formulation.

More preferably, the monopersulfate is added at a concentration range of about 1-20% w/v, the carbonate-type buffer within a range of 0.05-20% w/v, the ketone is present at a concentration range of 0.1-20% v/v and, when present, the co-solvent(s) are present in a concentration range of 0.5-20% v/v and the surfactant(s) are present at a concentration range of 0.01-5% w/v. Solubility of each element will vary according to temperature and presence of other solvents in solution.

The dioxirane-producing formulations of this invention are effective over a wide range of temperatures that would be encountered in field operations. Although some dioxirane of the formulation could volatilize upon initial contact with a hot surface, the cooling effect occurring between the CBW contaminated material and application of the dioxirane solution will allow the decontamination process to effectively continue.

Dioxirane can be generated and collected within a contained system, with a slight diminishing of effectiveness towards CW simulant degradation over time. With regards to the monopersulfate component, only <1% active oxygen content is lost per month upon storage of the solid compound, whereas stability declines over time when placed in a bicarbonate buffered aqueous solution slightly above neutral conditions and up to about pH 9 where the minimum stability exists. For this reason, to minimize instability and degradation of the active monopersulfate and dioxirane components, the decontaminating solution of the present invention is therefore meant to be generated on-site within a short time (less than 1 hour) prior to use.

Specific equipment will be required to mix and deliver sufficient volumes of the decontaminating solution within a short period of time, similar to basic fire-fighting equipment outfitted with a spray delivery device that can dispense a significant volume of decontaminant over a large surface area. Examples include the U.S. Army ABC-M12A1 skid-mounted decontamination apparatus, which is capable of supporting foam, aqueous or deicing-like solutions; and the M17 transportable decontaminating system that can draw water from a nearby source to dispense a spray to equipment and vehicles. The availability of a water source, or to transport carbonated-like buffered water, will be a requirement for use of the present invention, as well as separate containments of solid monopersulfate and ketone.

The following specific examples are intended to illustrate the effectiveness of the invention.

Example 1

A dimethyldioxirane (DMDO) formulation was compared against control systems, as well as to a bicarbonate-buffered monopersulfate (Oxone®) system, to test effectiveness in degrading a VX agent stimulant, Demeton (175 nmols). The components utilized for corresponding 15 mL batch systems at pH 7 and 22° C. were based on concentrations in tap water of 1.45% w/v Oxone®, and/or 0.9% w/v sodium bicarbonate, and/or 5% v/v acetone, as applicable. The test systems consisted of Acetone in water (ACE), Acetone & bicarbonate in water (ACEBICARB), minimum and maximum amounts of potassium sulfate in bicarbonate buffer (minSALT & max-SALT), a bicarbonate buffered Oxone® (OXONE) and the formulation of the present invention (DMDO), generated by combining acetone with Oxone®.

| Time | Simulant Mass (nmols) | | | | | |
|---|---|---|---|---|---|---|
| (mins.) | ACE | ACEBICARB | minSALT | maxSALT | OXONE | DMDO |
| 0.333 | 170 | 177 | 184 | 145 | 0.16 | bd |
| 0.83 | 161 | 171 | 209 | 159 | 0.22 | bd |
| 1.5 | 166 | 161 | 180 | 149 | 0.53 | bd |
| 3 | 159 | 145 | 181 | 150 | 0.27 | bd |
| 5 | 171 | 161 | 181 | 150 | 0.23 | bd |
| Control Avg. | 165 | 163 | 187 | 150 | — | — |
| Std. Dev. | 5 | 12 | 13 | 5 | — | — |
| Rel. Std. Dev (%) | 3 | 7 | 7 | 3 | — | — | bd = below detection

As expected, controls were unreactive towards the agent simulant. The buffered Oxone® solution, with ketone absent, was not as effective at achieving degradation of the simulant below limits of detection as compared to reactivity observed by the DMDO formulation described by the present invention.

Example 2

A highly concentrated level of VX simulant, Demeton (140 umols) was tested in the presence of a DMDO-producing formulation that contained co-solvent and surfactant, and compared similarly against controls. Components for the corresponding 5.6 mL test systems were used at concentrations of 10% w/v Oxone®, 7% w/v sodium bicarbonate, and/or 20% v/v acetone, as applicable, all at pH 7.6 and 22° C. Test systems were 'SULFATE' containing maximum amounts of potassium sulfate in bicarbanate buffer, 'OXONE' present in bicarbonate buffer, and 'DMDO' generated as described in the present invention. Each test system included 10% v/v acetonitrile as co-solvent and 0.1% TBAHS as surfactant.

| Time | Simulant Mass (mmol) | | |
|---|---|---|---|
| (mins.) | SULFATE | OXONE | DMDO |
| 2 | 0.151 | 0.113 | 0.001 |
| 5 | 0.144 | 0.065 | 0.001 |
| 10 | 0.128 | 0.062 | 0.003 |
| 20 | 0.137 | 0.052 | 0.001 |
| Control Avg. | 0.140 | — | — |
| Std. Dev. | 0.010 | — | — |
| Rel. Std. Dev. (%) | 7 | — | — |

Again, DMDO was considerably more effective at degrading the simulant as compared to buffered Oxone®.

The inventors also noted other observations at different sampling times with real agents of HD, VX, and GD (Soman) using a dilute DMDO formulation. At 20 minutes sampling time, HD indicated complete degradation mainly to the corresponding sulfone derivative as the main product, with minor divinyl mustard products. At 40 minute sampling, VX and degradation products consisting of non-toxic ethyl-methyl phosphoric acid (EMPA) and N-oxide were observed. GD (Soman) in the presence of the dioxirane solution of the present invention resulted in the formation of the non-toxic GD-acid degradation product. The examples provided of agent tests were conducted in which dioxirane in the buffered monopersulfate solution of the present invention was significantly limited compared to the amount of agent spiked into the system.

Biological viruses and bacteria have been demonstrated to undergo rapid kill (up to 7-logs, i.e. 99.99999%) within seconds in the presence of the DMDO formulation of the present invention. Testing of a Bacillus anthracis 'wet' spore simulant, Bacillus thuringiensis, was shown to undergo nearly 7-log kill in 10 minutes when exposed to DMDO. In comparison, a 'dry' preparation of these highly resistant spores also achieved 7-log kill within 20 minutes of exposure by DMDO. Bicarbonate-buffered Oxone® alone was only capable of achieving 40% kill at 20 minutes reaction time.

Example 3

A DMDO formulation was tested against both a bicarbonate buffered (pH 7) and unbuffered (pH 2) Oxone® system for inactivating a $2 \times 10^7$ anthrax spore simulant, Bacillus globigii. Corresponding components for each 10 mL batch system were based on concentrations of 10% w/v Oxone®, 4.2% w/v sodium bicarbonate, and, in the case of the DMDO formulation, 10% v/v acetone, all in deionized water. Spores were placed into each system at different temperatures and exposed for 15 minutes.

| Temperature | % Inactivation of Spores @ 15 Minutes | | |
|---|---|---|---|
| ° C. | DMDO, pH 7 | OXONE, pH 7 | OXONE, pH 2 |
| −3 | 98.55 | 50 | 99.69 |
| 4 | 99.993 | 87.92 | 99.75 |
| 25 | 100 | 26.67 | 94.33 |
| 55 | 90 | 100 | 99.84 |

A virus simulant was also exposed to a dioxirane-producing formulation of the present invention between 4° C. and 50° C., demonstrating complete kill at each temperature examined.

We claim:

1. A composition consisting of:
   water;
   one or more monopersulfate compounds;
   one or more buffers selected from the group consisting of alkali metal salts of bicarbonate and carbonate;
   one or more co-solvents, wherein at least one of the co-solvents is selected from the group consisting of acetonitrile, tert-butanol, propylene carbonate, propylene glycol, and polypropylene glycol; and
   one or more ketones, at least one of said ketones being selected from the group consisting of acetone, 2-butanone, 2-pentanone, 2-hydroxy-4-methyl-2-pentanone, hexafluoroacetone, trifluoroacetone, acetophenone, camphorsulfonic acid, and levulinic acid,
   wherein the composition has a pH of from 5 to about 9 and is formulated to achieve in situ generation of dioxirane.

2. The composition of claim 1, wherein at least one of the monopersulfate compounds is an alkali metal salt form of monopersulfate.

3. The composition of claim 1, wherein at least one of the monopersulfate compounds is selected from the group consisting of alkali metal salt forms of peroxymonosulfuric acid alone or in combination with the alkali metal salts of sulfuric or persulfuric acid.

4. The composition of claim 1, wherein the monopersulfate is in the form of a potassium triple salt compound generally represented by the formula $2KHSO_5 \cdot KHSO_4 \cdot K_2SO_4$.

5. The composition of claim 1, 2, 3 or 4, wherein the monopersulfate compound(s) are present in a concentration range of about 0.1-40% w/v, the buffer(s) are present in a concentration range of about 0.05-20% w/v, the co-solvent(s) are present in a concentration range of about 0.01-40% v/v, and the ketone(s) are present in a concentration range of about 0.1-40% v/v.

6. The composition of claim 1, 2, 3, or 4 wherein the monopersulfate compound(s) are present in a concentration range of about 1-20% w/v, the buffer(s) are present in a concentration range of about 0.05-20% w/v, the co-solvent(s) are present in a concentration range of about 0.5-20% v/v, and the ketone(s) are present in a concentration range of about 0.1-20% v/v.

7. A composition consisting of:
   water;
   one or more monopersulfate compounds;
   one or more buffers selected from the group consisting of alkali metal salts of bicarbonate and carbonate;
   one or more surfactants; and
   one or more ketones, at least one of said ketones being selected from the group consisting of acetone, 2-butanone, 2-pentanone, 2-hydroxy-4-methyl-2-pentanone, hexafluoroacetone, trifluoroacetone, acetophenone, camphorsulfonic acid, and levulinic acid,
   wherein the composition has a pH of from 5 to about 9 and is formulated to achieve in situ generation of dioxirane.

8. The composition of claim 7, wherein at least one of the monopersulfate compounds is an alkali metal salt form of monopersulfate.

9. The composition of claim 7, wherein at least one of the monopersulfate compounds is selected from the group consisting of alkali metal salt forms of peroxymonosulfuric acid alone or in combination with the alkali metal salts of sulfuric or persulfuric acid.

10. The composition of claim 7, wherein the monopersulfate is in the form of a potassium triple salt compound generally represented by the formula $2KHSO_5 \cdot KHSO_4 \cdot K_2SO_4$.

11. The composition of claim 7, wherein at least one of the wherein at least one of the surfactants is selected from the group consisting of tetrabutylammonium hydrogen sulfate (TBAHS), cetyltrimethylammonium (CTMA) chloride, and octyl phenol ethoxylate.

12. The composition of claim 7, 8, 9, 10, or 11, wherein the monopersulfate compound(s) are present in a concentration range of about 0.1-40% w/v, the buffer(s) are present in a concentration range of about 0.05-20% w/v, the surfactant(s) are present in a concentration range of about 0.01-15% w/v, and the ketone(s) are present in a concentration range of about 0.1-40% v/v.

13. The composition of claims 7, 8, 9, 10, or 11, wherein the monopersulfate compound(s) are present in a concentration range of about 1-20% w/v, the buffer(s) are present in a concentration range of about 0.05-20% w/v, the surfactant(s) are present in a concentration range of about 0.01-5% w/v, and the ketone(s) are present in a concentration range of about 0.1-20% v/v.

14. A composition consisting of:
    water;
    one or more monopersulfate compounds;
    one or more buffers selected from the group consisting of alkali metal salts of bicarbonate and carbonate;
    one or more co-solvents;
    one or more surfactants; and
    one or more ketones, at least one of said ketones being selected from the group consisting of acetone, 2-butanone, 2-pentanone, 2-hydroxy-4-methyl-2-pentanone, hexafluoroacetone, trifluoroacetone, acetophenone, camphorsulfonic acid, and levulinic acid,
    wherein the composition has a pH of from 5 to about 9 and is formulated to achieve in situ generation of dioxirane.

15. The composition of claim 14, wherein at least one of the monopersulfate compounds is an alkali metal salt form of monopersulfate.

16. The composition of claim 14, wherein at least one of the monopersulfate compounds is selected from the group consisting of alkali metal salt forms of peroxymonosulfuric acid alone or in combination with the alkali metal salts of sulfuric or persulfuric acid.

17. The composition of claim 14, wherein the monopersulfate is in the form of a potassium triple salt compound generally represented by the formula $2KHSO_5 \cdot KHSO_4 \cdot K_2SO_4$.

18. The composition of claim 14, wherein at least one of the co-solvents is selected from the group consisting of acetonitrile, tert-butanol, propylene carbonate, propylene glycol, and polypropylene glycol.

19. The composition of claim 14, wherein at least one of the wherein at least one of the surfactants is selected from the group consisting of tetrabutylammonium hydrogen sulfate (TBAHS), cetyltrimethylammonium (CTMA) chloride, and octyl phenol ethoxylate.

20. The composition of claim 14, 15, 16, 17, 18 or 19, wherein the monopersulfate compound(s) are present in a concentration range of about 0.1-40% w/v, the buffer(s) are present in a concentration range of about 0.05-20% w/v, the co-solvent(s) are present in a concentration range of about 0.01-40% v/v, the surfactant(s) are present in a concentration range of about 0.01-15% w/v, and the ketone(s) are present in a concentration range of about 0.1-40% v/v.

21. The composition of claims 14, 15, 16, 17, 18 or 19, wherein the monopersulfate compound(s) are present in a concentration range of about 1-20% w/v, the buffer(s) are present in a concentration range of about 0.05-20% w/v, the co-solvent(s) are present in a concentration range of about 0.5-20% v/v, the surfactant(s) are present in a concentration range of about 0.01-5% w/v, and the ketone(s) are present in a concentration range of about 0.1-20% v/v.

* * * * *

UNITED STATES PATENT AND TRADEMARK OFFICE
CERTIFICATE OF CORRECTION

PATENT NO. : 7,582,594 B2  Page 1 of 1
APPLICATION NO. : 10/687864
DATED : September 1, 2009
INVENTOR(S) : Delcomyn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 375 days.

Signed and Sealed this

Fourteenth Day of September, 2010

David J. Kappos
*Director of the United States Patent and Trademark Office*